United States Patent
Li

(10) Patent No.: US 8,050,758 B2
(45) Date of Patent: *Nov. 1, 2011

(54) METHOD AND APPARATUS FOR SELECTING AND TIMING ANTI-TACHYARRHYTHMIA PACING USING CARDIAC CYCLE LENGTH STABILITY

(75) Inventor: Dan Li, Shoreview, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 12/829,218

(22) Filed: Jul. 1, 2010

(65) Prior Publication Data

US 2010/0268290 A1 Oct. 21, 2010

Related U.S. Application Data

(62) Division of application No. 11/275,696, filed on Jan. 25, 2006, now Pat. No. 7,761,154.

(51) Int. Cl.
*A61N 1/362* (2006.01)
(52) U.S. Cl. ............................................... 607/14
(58) Field of Classification Search .................. 607/4, 9, 607/14
See application file for complete search history.

(56) References Cited

U.S. PATENT DOCUMENTS

| | | | |
|---|---|---|---|
| 4,830,006 A | 5/1989 | Haluska et al. |
| 5,163,429 A | 11/1992 | Cohen |
| 5,183,040 A | 2/1993 | Nappholz et al. |
| 5,788,717 A | 8/1998 | Mann et al. |
| 5,797,395 A | 8/1998 | Martin |
| 5,897,575 A | 4/1999 | Wickham |
| 5,978,707 A | 11/1999 | Krig et al. |
| 5,999,854 A | 12/1999 | Deno et al. |
| 6,101,414 A | 8/2000 | Kroll |
| 6,493,579 B1 | 12/2002 | Gilkerson et al. |
| 6,522,925 B1 | 2/2003 | Gilkerson et al. |
| 6,654,639 B1 | 11/2003 | Lu |
| 6,775,572 B2 | 8/2004 | Zhu et al. |
| 6,885,890 B2 | 4/2005 | Spinelli et al. |
| 7,010,344 B2 | 3/2006 | Burnes et al. |
| 7,228,173 B2 | 6/2007 | Cazares |
| 7,277,750 B2 | 10/2007 | Perschbacher et al. |
| 2003/0083703 A1 | 5/2003 | Zhu et al. |

(Continued)

FOREIGN PATENT DOCUMENTS

WO WO-9519806 A1 7/1995

(Continued)

OTHER PUBLICATIONS

"U.S. Appl. No. 11/275,696, Non Final Office Action mailed Aug. 5, 2009", 12 pgs.

(Continued)

*Primary Examiner* — Carl H Layno
*Assistant Examiner* — Allen Porter, Jr.
(74) *Attorney, Agent, or Firm* — Schwegman, Lundberg & Woessner, P.A.

(57) ABSTRACT

An implantable medical device delivers anti-tachyarrhythmia therapies including anti-tachyarrhythmia pacing (ATP). When a tachyarrhythmia episode is detected, the implantable medical device analyzes cardiac cycle length stability to determine whether and/or when to deliver an ATP. In one embodiment, the cardiac cycle length stability is measured by existence of stable ventricular tachyarrhythmia clusters (SVTCs) during the tachyarrhythmia episode. Each SVTC includes at least a specified minimum number of heart beats over which the cardiac cycle lengths meet a stability criterion.

21 Claims, 6 Drawing Sheets

U.S. PATENT DOCUMENTS

| | | |
|---|---|---|
| 2003/0208240 A1 | 11/2003 | Pastore et al. |
| 2004/0093035 A1 | 5/2004 | Schwartz et al. |
| 2004/0220634 A1 | 11/2004 | Belk |
| 2004/0220636 A1 | 11/2004 | Burnes |
| 2004/0230129 A1 | 11/2004 | Haefner |
| 2005/0149135 A1 | 7/2005 | Krig et al. |
| 2005/0222629 A1 | 10/2005 | Perschbacher et al. |
| 2007/0142866 A1 | 6/2007 | Li |

FOREIGN PATENT DOCUMENTS

| | | |
|---|---|---|
| WO | WO-2007/078421 A2 | 7/2007 |

OTHER PUBLICATIONS

"U.S. Appl. No. 11/275,696, Advisory Action mailed May 21, 2009", 5 pgs.

"U.S. Appl. No. 11/275,696, Examiner Interview Summary mailed Dec. 7, 2009", 4 pgs.

"U.S. Appl. No. 11/275,696, Final Office Action mailed Mar. 10, 2009", 13 pgs.

"U.S. Appl. No. 11/275,696, Non-Final Office Action mailed Aug. 28, 2008", 13 pgs.

"U.S. Appl. No. 11/275,696, Notice of Allowance mailed Mar. 15, 2010", 6 pgs.

"U.S. Appl. No. 11/275,696, Response filed May 11, 2009 to Final Office Action mailed Mar. 10, 2009", 10 pgs.

"U.S. Appl. No. 11/275,696, Response filed Jun. 9, 2009 to Advisory Action mailed May 21, 2009", 10 pgs.

"U.S. Appl. No. 11/275,696, Response filed Aug. 11, 2008 to Restriction Requirement mailed Jul. 9, 2008", 13 pgs.

"U.S. Appl. No. 11/275,696, Response filed Nov. 25, 2008 to Non Final Office Action mailed Aug. 28, 2008", 9 pgs.

"U.S. Appl. No. 11/275,696, Response filed Dec. 7, 2009 to Non Final Office Action mailed Aug. 5, 2009", 12 pgs.

"U.S. Appl. No. 11/275,696, Restriction Requirement mailed Jul. 9, 2008", 7 pgs.

"International Application Serial No. PCT/US2006/043459, International Search Report mailed Oct. 23, 2007", 7 pgs.

"International Application Serial No. PCT/US2006/043459, Partial International Search Report mailed Mar. 14, 2007", 6 pgs.

"International Application Serial No. PCT/US2006/043459, Written Opinion mailed Oct. 23, 2007", 13 pgs.

Steinbach, K. K, et al., "Hemodynamics during ventricular tachyarrhythmias", *American Heart Journal*, 127(4, Part 2), (Apr. 1994), 1102-1106.

METHOD AND APPARATUS FOR SELECTING AND TIMING ANTI-TACHYARRHYTHMIA PACING USING CARDIAC CYCLE LENGTH STABILITY

CROSS REFERENCE TO RELATED APPLICATION

This application is a divisional of U.S. application Ser. No. 11/275,696, filed Jan. 25, 2006, now issued as U.S. Pat. No. 7,761,154, which is hereby incorporated by reference in its entirety.

TECHNICAL FIELD

This document relates generally to cardiac rhythm management (CRM) systems and particularly, but not by way of limitation, to a system that controls the selection and timing of anti-tachyarrhythmia pacing (ATP) therapy based on cardiac cycle length stability.

BACKGROUND

Tachyarrhythmias are abnormal heart rhythms characterized by a rapid heart rate. Tachyarrhythmias generally include supraventricular tachyarrhythmia (SVT, including atrial tachyarrhythmia, AT) and ventricular tachyarrhythmia (VT). Fibrillation is a form of tachyarrhythmia further characterized by an irregular heart rhythm. In a normal heart, the sinoatrial node, the heart's predominant natural pacemaker, generates electrical impulses, called action potentials, that propagate through an electrical conduction system to the atria and then to the ventricles of the heart to excite the myocardial tissues. The atria and ventricles contract in the normal atrioventricular sequence and synchrony to result in efficient blood-pumping functions indicated by a normal hemodynamic performance. VT occurs when the electrical impulses propagate along a pathologically formed self-sustaining conductive loop within the ventricles or when a natural pacemaker in a ventricle usurps control of the heart rate from the sinoatrial node. When the atria and the ventricles become dissociated during VT, the ventricles may contract before they are properly filed with blood, resulting in diminished blood flow throughout the body. This condition becomes life-threatening when the brain is deprived of sufficient oxygen supply. Ventricular fibrillation (VF), in particular, stops blood flow within seconds and, if not timely and effectively treated, causes immediate death. In very few instances a heart recovers from VF without treatment.

Cardioversion and defibrillation are used to terminate most tachyarrhythmias, including AT, VT, and VF. An implantable cardioverter/defibrillator (ICD) is a cardiac rhythm management (CRM) device that delivers an electric shock to terminate a detected tachyarrhythmia episode by depolarizing the entire myocardium simultaneously and rendering it refractory.

Another type of electrical therapy for tachyarrhythmia is anti-tachyarrhythmia pacing (ATP). In ATP, the heart is competitively paced in an effort to interrupt the reentrant loop causing the tachyarrhythmia. An exemplary ICD includes ATP and defibrillation capabilities so that ATP is delivered to the heart when a non-fibrillation VT is detected, while a defibrillation shock is delivered when fibrillation occurs. Although cardioversion and/or defibrillation are effective in terminating tachyarrhythmia, they consume a large amount of power and result in patient discomfort owing to the high voltage of the shock pulses. It is desirable, therefore, for the ICD to use ATP to terminate a tachyarrhythmia whenever possible.

The efficacy of ATP in terminating tachyarrhythmia depends on the type of the tachyarrhythmia and the timing of ATP delivery. To be effective, an ATP therapy is to be delivered to the heart during an excitable gap in the reentrant loop. Inaccurate timing of an ATP delivery will contribute to the failure in terminating tachyarrhythmia using ATP.

For these and other reasons, there is a need for determining whether and when to deliver an ATP therapy.

SUMMARY

An implantable medical device delivers anti-tachyarrhythmia therapies including anti-tachyarrhythmia pacing (ATP). When a tachyarrhythmia episode is detected, the implantable medical device analyzes cardiac cycle length stability to determine whether and/or when to deliver an ATP. In one embodiment, the cardiac cycle length stability is measured by existence of stable ventricular tachyarrhythmia clusters (SVTCs) during the tachyarrhythmia episode. Each SVTC includes at least a specified minimum number of heart beats over which the cardiac cycle lengths meet a stability criterion.

In one embodiment, an implantable medical device includes a sensing circuit, a pacing output, a tachyarrhythmia detector, a tachyarrhythmia classifier, a primary duration timer, a cycle length stability analyzer, a secondary duration timer, and an ATP controller. The sensing circuit senses a cardiac signal. The pacing output circuit delivers pacing pulses. The tachyarrhythmia detector detects a tachyarrhythmia episode using the cardiac signal. The tachyarrhythmia classifier classifies the detected tachyarrhythmia episode. The primary duration timer initiates a primary duration when the tachyarrhythmia episode is detected. The cycle length stability analyzer analyzes stability of cardiac cycle lengths using the cardiac signal. The secondary duration timer controls an initiation of a secondary duration using the stability of cardiac cycle lengths analyzed during the primary duration and the classification of the detected tachyarrhythmia episode. The ATP controller controls the delivery of the pacing pulses according to an ATP mode using the stability of cardiac cycle lengths analyzed during the primary duration, a stability of cardiac cycle lengths analyzed during the secondary duration, and the classification of the detected tachyarrhythmia episode.

In one embodiment, a method for controlling ATP is provided. A cardiac signal is sensed. A tachyarrhythmia episode is detected using the cardiac signal. The detected tachyarrhythmia episode is classified. A primary duration is initiated when the tachyarrhythmia episode is detected. The stability of cardiac cycle lengths is analyzed during the primary duration. The initiation of a secondary duration is controlled using the stability of cardiac cycle lengths analyzed during the primary duration and the classification of the detected tachyarrhythmia episode. The stability of cardiac cycle lengths is analyzed during the second duration if the secondary duration is initiated. A delivery of pacing pulses is controlled according to an ATP mode using the stability of cardiac cycle lengths analyzed during the primary duration, the stability of cardiac cycle lengths analyzed during the secondary duration if the secondary duration is initiated, and the classification of the detected tachyarrhythmia episode.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

The drawings, which are not necessarily drawn to scale, illustrate generally, by way of example, but not by way of limitation, various embodiments discussed in the present document.

DETAILED DESCRIPTION

Figure 1:
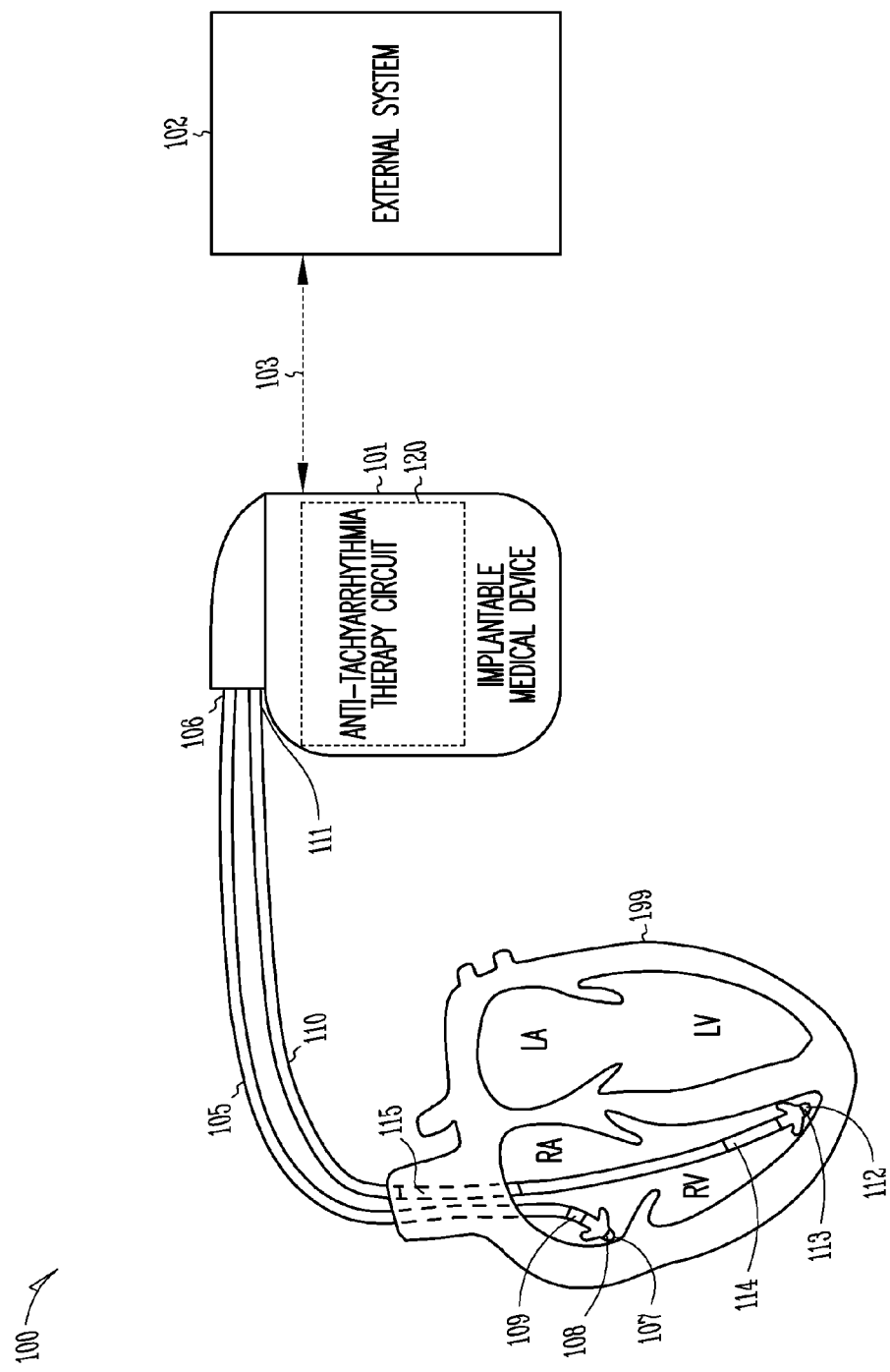
FIG. 1 is an illustration of an embodiment of a cardiac rhythm management (CRM) system including an implantable medical device that selects and times anti-tachyarrhythmia therapies using cardiac cycle length stability and portions of an environment in which the CRM system operates.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description provides examples, and the scope of the present invention is defined by the appended claims and their legal equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this documents and those documents so incorporated by reference, the usage in the incorporated reference(s) should be considered supplementary to that of this document; for irreconcilable inconsistencies, the usage in this document controls.

It should be noted that references to "an", "one", or "various" embodiments in this document are not necessarily to the same embodiment, and such references contemplate more than one embodiment.

The relationship between a heart rate and a cardiac cycle length (also known as cardiac interval), as used in this document, is the relationship between a frequency and its corresponding period. If a heart rate is given in beats per minute (bpm), its corresponding cardiac cycle length in milliseconds is calculated by dividing 60,000 by the heart rate (where 60,000 is the number of milliseconds in a minute). Any process, such as a comparison, using a heart rate is to be modified accordingly when a cardiac cycle length is used instead. For example, if a tachyarrhythmia is detected when the ventricular rate exceeds a tachyarrhythmia threshold rate, an equivalent process is to detect the tachyarrhythmia when the ventricular cycle length (also known as ventricular interval) falls below a tachyarrhythmia threshold interval. The appended claims should be construed to cover such variations.

This document discusses a cardiac rhythm management (CRM) system that delivers anti-tachyarrhythmia therapies including anti-tachyarrhythmia pacing (ATP) and controls the anti-tachyarrhythmia therapies, including selection and delivery time of the ATP, based on cardiac cycle length stability. An ATP therapy is most effective when delivered during an "excitable gap" after ventricular repolarization (T wave) and before ventricular depolarization (QRS complex). The delivery of an ATP therapy is typically initiated at the end of a "coupled interval" (CI), which starts with a ventricular depolarization and has a length intended to end during the excitable gap. When the CI is calculated as a percentage of a cardiac cycle length, such as an average of time intervals between two consecutive ventricular depolarizations, the ATP therapy is most effective when delivered while the cardiac cycle lengths are substantially stable (with small variations). When the cardiac cycle lengths are substantially unstable, the ATP may not be effective in terminating a tachyarrhythmia episode because of the difficulty in ensuring that the ATP therapy is delivered during the excitable gap. One solution is to deliver a more aggressive therapy, such as cardioversion/defibrillation, when the cardiac cycle lengths are substantially unstable at the time of a scheduled ATP delivery. However, it is still possible to use ATP, when it is preferable over the more aggressive therapy, by searching for a relatively short period during which the cardiac cycle lengths are substantially stable. That is, when the cardiac cycle lengths during the tachyarrhythmia episode is generally unstable over a relatively long period, an ATP therapy may still be effective if delivered when the cardiac cycle lengths are substantially stable over a relatively short period (such as a few consecutive heart beats), if such a relatively short period exists and is detectable.

The present CRM system detects stable ventricular tachyarrhythmia clusters (SVTCs), each including at least a specified minimum number of consecutive heart beats over which the cardiac cycle lengths meet a stability criterion. An ATP therapy is selected when at least one SVTC is detected and delivered upon the detection of an SVTC. In response to the detection of a tachyarrhythmia episode based on heart rate, a primary duration is initiated. The detected tachyarrhythmia is classified, such as by its origin, and the SVTCs are detected, during the primary duration. If the detected tachyarrhythmia is classified as ventricular tachyarrhythmia (VT), and the primary duration expires with an SVTC, an ATP therapy is delivered when the primary duration expires. If the detected tachyarrhythmia is classified as VT, but no SVTC is detected during the primary duration, a more aggressive therapy, such as a cardioversion/defibrillation therapy, is delivered. If the detected tachyarrhythmia is classified as VT, and at least one SVTC is detected during the primary duration, but the primary duration does not expire with an SVTC, a secondary (extended) duration is initiated. If the detected tachyarrhythmia is classified as supraventricular tachyarrhythmia (SVT), and at least one SVTC is detected during the primary duration, the secondary duration is initiated, after the primary duration expires, if and when the detected tachyarrhythmia becomes classified as VT. The ATP therapy is initiated when an SVTC is detected during the secondary duration. If no SVTC is detected during the secondary duration, a more aggressive therapy, such as a cardioversion/defibrillation therapy, is delivered when the secondary duration expires.

FIG. 1 is an illustration of one embodiment of a CRM system 100 and portions of the environment in which CRM system 100 operates. CRM system 100 includes an implantable medical device 101 that is electrically coupled to a heart 199 through one or more electrodes, such as on leads 105 and 110. An external system 102 communicates with implantable medical device 101 via a telemetry link 103.

Implantable medical device 101 delivers anti-tachyarrhythmia therapies including ATP and cardioversion/defibrillation therapies. In one embodiment, implantable medical device 101 is an implantable cardioverter/defibrillator (ICD) with cardiac pacing capabilities. In another embodiment, in addition to a pacemaker and a cardioverter/defibrillator, implantable medical device 101 further includes one or more of other monitoring and/or therapeutic devices such as a neural stimulator, a drug delivery device, and a biological therapy device. Implantable medical device 101 includes a hermetically sealed can housing an electronic circuit that senses physiological signals and delivers therapeutic electrical pulses. The hermetically sealed can also functions as an electrode for sensing and/or pulse delivery purposes. In one embodiment, as illustrated in FIG. 1, the electronic circuit senses at least an atrial electrogram and a ventricular electrogram from heart 199 and delivers pacing and cardioversion/defibrillation pulses to heart 199. Lead 105 is typically a pacing lead that includes a proximal end 106 connected to implantable medical device 101 and a distal end 107 placed in the right atrium (RA) of heart 199. A pacing-sensing electrode 108 is located at distal end 107. Another pacing-sensing electrode 109 is located near distal end 107. Electrodes 108 and 109 are electronically connected to implantable medical device 101 via separate conductors in lead 105 to allow sensing of the atrial electrogram and/or delivery of atrial pacing pulses. Lead 110 is typically a defibrillation lead that includes a proximal end 111 connected to implantable medical device 101 and a distal end 112 placed in the right ventricle (RV) of heart 199. A pacing-sensing electrode 113 is located at distal end 112. A defibrillation electrode 114 is located near distal end 112 but electrically separated from pacing-sensing electrode 113. Another defibrillation electrode 115 is located at a distance from distal end 112 for supraventricular placement. Electrodes 113, 114, and 115 are electrically connected to implantable medical device 101 via separate conductors in lead 110. Electrode 113 allows sensing of the ventricular electrogram and/or delivery of ventricular pacing pulses. Electrodes 114 and 115 allow delivery of ventricular cardioversion/defibrillation pulses.

Implantable medical device 101 includes an anti-tachyarrhythmia therapy circuit 120 that selects and times anti-tachyarrhythmia therapies using cardiac cycle length stability. In various embodiments, anti-tachyarrhythmia therapy circuit 120 provides implantable medical device 101 with ATP and cardioversion/defibrillation therapy modes. An ATP therapy mode is selected when the cardiac cycle length is determined to be substantially stable for at least a short period that last over a plurality of heart beats. The delivery of the selected ATP therapy is initiated while the cardiac cycle length is substantially stable. In one embodiment, the cardiac cycle stability is measured by the detection of SVTC. Various embodiments of system 120 are discussed below, with reference to FIGS. 2 and 3. In various embodiments, implantable medical device 101 also includes one or more of other cardiac electrical therapy circuits such as an anti-bradyarrhythmia circuit, a cardiac resynchronization therapy (CRT) circuit, a cardiac remodeling control therapy (RCT) circuit.

External system 102 allows for programming of implantable medical device 101 and receives signals acquired by implantable medical device 101. In one embodiment, external system 102 includes a programmer. In another embodiment, external system 102 is a patient management system including an external device in proximity of implantable medical device 101, a remote device in a relatively distant location, and a telecommunication network linking the external device and the remote device. The patient management system allows access to implantable medical device 101 from a remote location, such as for monitoring patient status and adjusting therapies. Telemetry link 103 is a wireless communication link providing for bidirectional data transmission between implantable medical device 101 and external system 102. In one embodiment, telemetry link 103 is an inductive telemetry link. In an alternative embodiment, telemetry link 103 is a far-field radio-frequency telemetry link. Telemetry link 103 provides for data transmission from implantable medical device 101 to external system 102. This may include, for example, transmitting real-time physiological data acquired by implantable medical device 101, extracting physiological data acquired by and stored in implantable medical device 101, extracting therapy history data stored in implantable medical device 101, and extracting data indicating an operational status of implantable medical device 101 (e.g., battery status and lead impedance). Telemetry link 103 also provides for data transmission from external system 102 to implantable medical device 101. This may include, for example, programming implantable medical device 101 to acquire physiological data, programming implantable medical device 101 to perform at least one self-diagnostic test (such as for a device operational status), programming implantable medical device 101 to enable an available monitoring or therapeutic function (such as ATP), and programming implantable medical device 101 to adjust therapeutic parameters such as pacing and/or cardioversion/defibrillation parameters.

Figure 2:
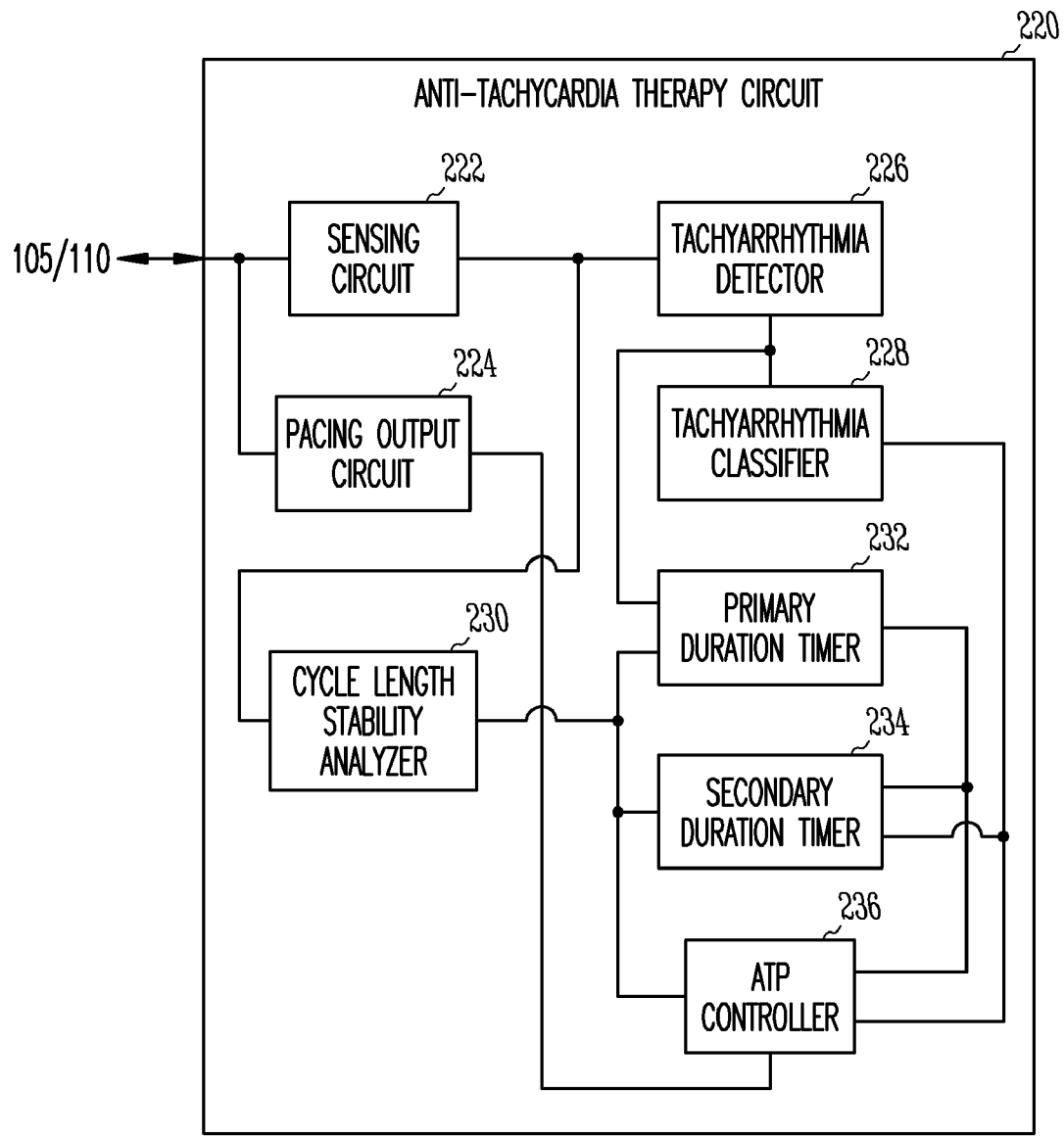
FIG. 2 is a block diagram illustrating an embodiment of an anti-tachyarrhythmia therapy circuit of the implantable medical device.

FIG. 2 is a block diagram illustrating an embodiment of an anti-tachyarrhythmia therapy circuit 220, which is a specific embodiment of anti-tachyarrhythmia therapy circuit 120. Anti-tachyarrhythmia therapy circuit 220 includes a sensing circuit 222, a pacing output circuit 224, a tachyarrhythmia detector 226, a tachyarrhythmia classifier 228, a cycle length stability analyzer 230, a primary duration timer 232, a secondary duration timer 234, and an ATP controller 236.

Sensing circuit 222 senses one or more cardiac signals through one or more leads such as leads 105 and 110. Pacing output circuit 224 delivers pacing pulses to the heart through one or more leads such as leads 105 and 110. Tachyarrhythmia detector 226 detects a tachyarrhythmia episode using the one or more cardiac signals. Tachyarrhythmia classifier 228 classifies the detected tachyarrhythmia episode as one of predetermined types of tachyarrhythmia. Cycle length stability analyzer 230 analyzes the stability of cardiac cycle lengths indicated by the one or more cardiac signals.

In response to the detection of a tachyarrhythmia episode by tachyarrhythmia detector 226, primary duration timer 232 initiates a primary duration. Cycle length stability analyzer 230 monitors the stability of cardiac cycle lengths during the primary duration. The detected tachyarrhythmia episode is classified by tachyarrhythmia classifier 228 at the end of the primary duration. Secondary duration timer 234 controls the initiation of a secondary duration using the stability of the cardiac cycle lengths during the primary duration and the classification of the detected tachyarrhythmia episode. If the secondary duration is initiated, cycle length stability analyzer 230 monitors the stability of cardiac cycle lengths during the secondary duration. ATP controller 236 controls the delivery of the pacing pulses according to an ATP mode using the stability of the cardiac cycle lengths during the primary duration, the stability of the cardiac cycle lengths during the secondary duration, and the classification of the detected tachyarrhythmia episode.

Figure 3:
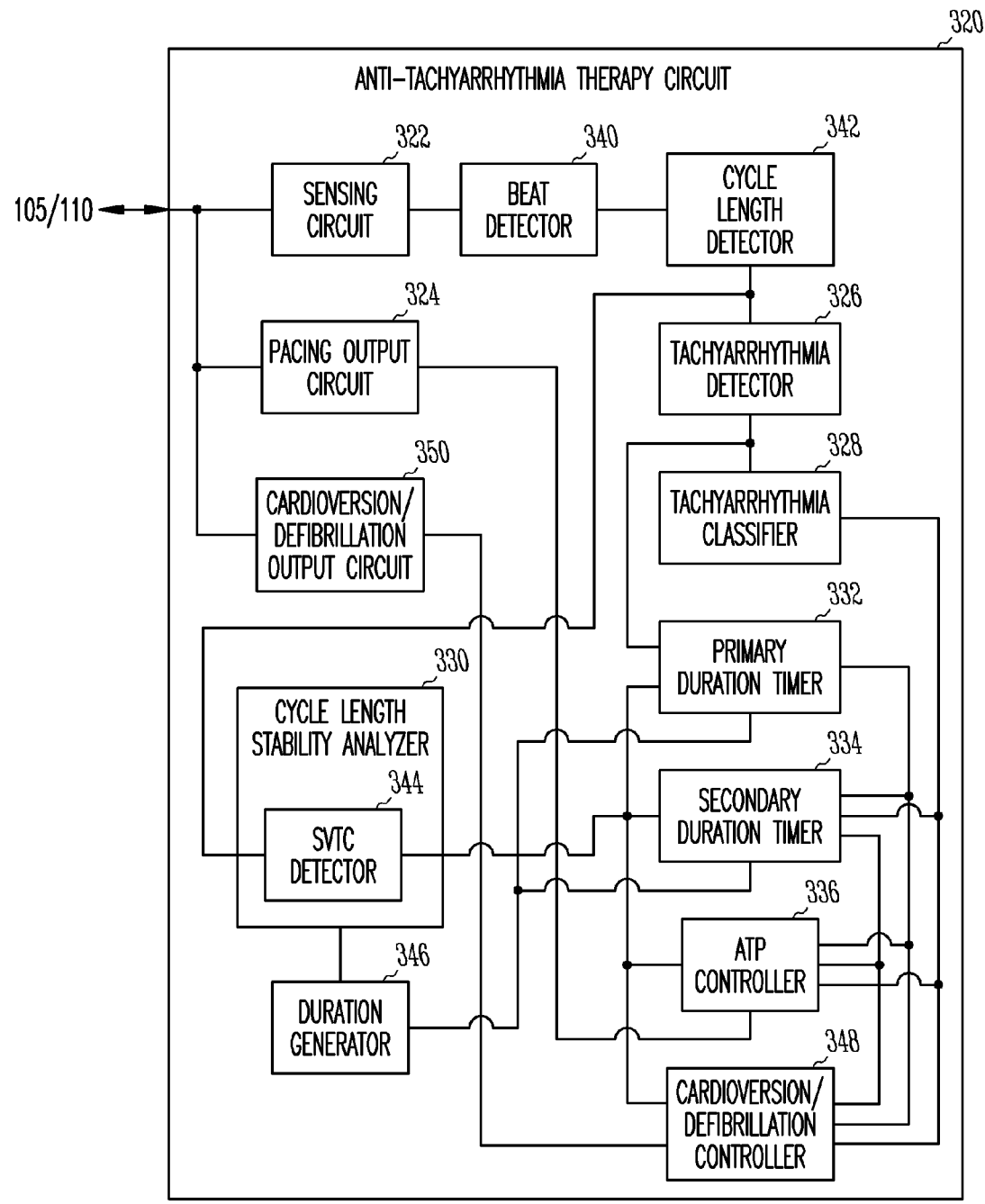
FIG. 3 is a block diagram illustrating a specific embodiment of the anti-tachyarrhythmia therapy circuit.

FIG. 3 is a block diagram illustrating an embodiment of an anti-tachyarrhythmia therapy circuit 320, which is a specific embodiment of anti-tachyarrhythmia therapy circuit 220. Anti-tachyarrhythmia therapy circuit 220 includes a sensing circuit 322, a beat detector 340, a cycle length detector 342, a tachyarrhythmia detector 326, a tachyarrhythmia classifier 328, a cycle length stability analyzer 330, a pacing output circuit 324, a cardioversion/defibrillation output circuit 350, a primary duration timer 332, a secondary duration timer 334, a duration generator 346, an ATP controller 336, and a cardioversion/defibrillation controller 348.

Sensing circuit 322 senses at least one cardiac signal. Beat detector 340 detects heart beats from the cardiac signal. Cycle length detector 342 detects cardiac cycle lengths each being a time interval between two consecutively detected heart beats. Tachyarrhythmia detector 328 detects a tachyarrhythmia episode using the cardiac cycle lengths. In one embodiment, tachyarrhythmia detector 326 declares a detection of the tachyarrhythmia episode using the cardiac cycle lengths and one or more tachyarrhythmia detection thresholds. Tachyarrhythmia classifier 328 classifies the detected tachyarrhythmia episode as one of predetermined types of tachyarrhythmia. In one embodiment, the predetermined types of tachyarrhythmia include VT and SVT. In a specific embodiment, sensing circuit 322 senses a ventricular electrogram through lead 110. Beat detector 340 detects ventricular depolarizations as the heart beats from the ventricular electrogram. Cycle length detector 342 detects ventricular cycle lengths (also referred to as ventricular intervals) each being a time interval between two consecutively detected ventricular depolarizations. Tachyarrhythmia detector 326 declares a detection of a VT episode when the ventricular cycle lengths fall within a VT detection zone defined by at least one tachyarrhythmia detection threshold. Tachyarrhythmia classifier 328 confirms the detection of the VT episode by continuously or periodically classifying the detected VT episode as one of VT and SVT by examining the ventricular cycle lengths and ventricular electrogram morphologies.

Pacing output circuit 324 deliver pacing pulses. To allow ventricular ATP, pacing output circuit 324 includes a ventricular pacing output to deliver ventricular pacing pulses through lead 110. Cardioversion/defibrillation output circuit 348 delivers cardioversion/defibrillation pulses. To terminate ventricular tachyarrhythmia, cardioversion/defibrillation output circuit 348 includes a ventricular cardioversion/defibrillation output to deliver ventricular cardioversion/defibrillation pulses through lead 110.

Cycle length stability analyzer 330 includes an SVTC detector 344 to analyze the stability of the cardiac cycle lengths by detecting SVTCs. SVTC detector 344 detects SVTCs from the cardiac signal sensed by circuit 322. The SVTCs each include at least a specified minimum number of consecutively detected heart beats over which the cardiac cycle lengths meet a specified stability criterion. When the specified minimum number of consecutive heart beats are detected during each of the SVTCs, SVTC detector 344 declares an SVTC detection. In one embodiment, the minimum number is specified in range of approximately 4 to 8, with approximately 5 being a specific example. In one embodiment, the minimum number is programmable. In one embodiment, SVTC detector 344 calculates a cycle-to-cycle variation that is the difference between cardiac cycle lengths associated with two consecutively detected heart beats, compares the cycle-to-cycle variation to a predetermined threshold, and declares the SVTC detection when the cycle-to-cycle variation is below the predetermined threshold for the specified minimum number of consecutively detected heart beats. In another embodiment, SVTC detector 344 calculates a running average of the cardiac cycle lengths, compares the cardiac cycle length associated with each of the consecutively detected heart beats to the running average of the cardiac cycle lengths, and declares the SVTC detection when the difference between the cardiac cycle length associated with each of the consecutively detected heart beats and the running average of the cardiac cycle lengths is within a predetermined margin for the specified minimum number of consecutively detected heart beats. In another embodiment, SVTC detector 344 analyzes a correlation between the morphology of the cardiac signal over each of the detected heart beats and a predetermined template morphology and declares the SVTC detection when the morphology of the cardiac signal over each of the detected heart beats substantially correlates to the predetermined template morphology for the specified minimum number of consecutively detected heart beats.

Primary duration timer 332 initiates a primary duration (T1) when the tachyarrhythmia episode is detected by tachyarrhythmia detector 326. In one embodiment, the primary duration is a programmed constant duration in a range of approximately 1 to 30 seconds, with approximately 5 seconds as a specific example. Secondary duration timer 334 controls an initiation of a secondary duration (T2) using the stability of the cardiac cycle lengths during the primary duration and the classification of the detected tachyarrhythmia episode. In one embodiment, if the tachyarrhythmia is classified as VT when the primary duration expires and the stable SVTC detector declares at least one SVTC detection during the primary duration, but the primary duration does not expire with a detected SVTC, secondary duration timer 334 initiates the secondary duration when the primary duration expires. If the tachyarrhythmia is classified as VT after the primary duration expires and the stable SVTC detector declares at least one SVTC detection during the primary duration, secondary duration timer 334 initiates the secondary duration when the tachyarrhythmia is classified as VT. In one embodiment, the second duration is a programmed constant duration in a range of approximately 1 to 10 seconds, with approximately 2.5 seconds as a specific example. In another embodiment, duration generator 346 produces the second duration based on at least one of the number of SVTCs detected during the primary duration and the size (number of beats) of each of the SVTCs detected during the primary duration. The length of the secondary duration is increased for each SVTC detected during the primary duration and for each heart beat detected during each SVTC detected during the primary duration.

ATP controller 336 controls the delivery of the pacing pulses according to an ATP mode using the stability of the cardiac cycle lengths during the primary duration, the stability of the cardiac cycle lengths during the secondary duration, and the classification of the detected tachyarrhythmia episode. The delivery of the pacing pulses according to the ATP mode includes a delivery of at least one burst of pacing pulses. In one embodiment, each burst of pacing pulses includes approximately 3 to 10 pacing pulses, with approximately 5 pacing pulses as a specific example, at a pacing rate of approximately 200 to 250 pulses per minute, with approximately 200 pulses per minute as a specific example. In one embodiment, ATP controller 336 initiates the ATP therapy when the primary duration expires if the tachyarrhythmia is classified as VT when the primary duration expires and the primary duration expires with an SVTC. If the secondary duration is initiated by secondary duration timer 334, ATP controller 336 initiates the ATP therapy when a detection of SVTC is declared during the secondary duration if the tachyarrhythmia is classified as VT when the SVTC is detected during the secondary duration. In one embodiment, ATP controller 336 calculates a coupling interval (CI) using a predetermined number of the cardiac cycle lengths detected during the SVTC. The coupling interval is the time interval between the last detected beat of the SVTC and the first pacing pulse of the ATP therapy. In a specific embodiment, ATP controller 336 calculates the coupling interval as a specified percentage of an average of the predetermined number of the cardiac cycle lengths detected during the SVTC.

If no SVTC is detected during the primary duration, or if no SVTC is detected when the primary duration expires and no SVTC is detected during the secondary duration, a therapy more aggressive than the ATP is selected. Examples of such more aggressive therapies include cardioversion/defibrillation and ATP before charge (ATP-BC), which are discussed below.

Cardioversion/defibrillation controller 348 controls a cardioversion/defibrillation therapy using the stability of the cardiac cycle lengths during the primary duration, the stability of the cardiac cycle lengths during the secondary duration, and the classification of the detected tachyarrhythmia episode. In one embodiment, cardioversion/defibrillation controller 348 initiates a delivery of the cardioversion/defibrillation therapy if the tachyarrhythmia is classified as VT when the primary duration expires and no SVTC is detected during the primary duration. If the secondary duration is initiated by secondary duration timer 334, cardioversion/defibrillation controller 348 initiates a delivery of the cardioversion/defibrillation therapy if the tachyarrhythmia is classified as VT when the second duration expires and no SVTC is detected during the second duration. ATP-BC provides for an attempt to terminate the detected tachyarrhythmia episode using ATP immediately before charging a defibrillation capacitor. The defibrillation capacitor stores energy for a cardioversion/defibrillation pulse and is charged for the delivery of each cardioversion/defibrillation pulse. An example of ATP-BC is discussed in U.S. Pat. No. 7,277,752, entitled "METHOD AND APPARATUS FOR ANTI-TACHYARRHYTHMIA PACING AND DEFIBRILLATION," filed on Apr. 2, 2004, assigned to Cardiac Pacemakers, Inc., which is incorporated herein by reference in its entirety. In one embodiment, ATP controller 336 initiates the delivery of an ATP-BC therapy if the tachyarrhythmia is classified as VT when the primary duration expires and no SVTC is detected during the primary duration. If the secondary duration is initiated by secondary duration timer 334, ATP controller 336 initiates the delivery of the ATP-BC therapy if the tachyarrhythmia is classified as VT when the second duration expires and no SVTC is detected during the second duration.

Figure 4:
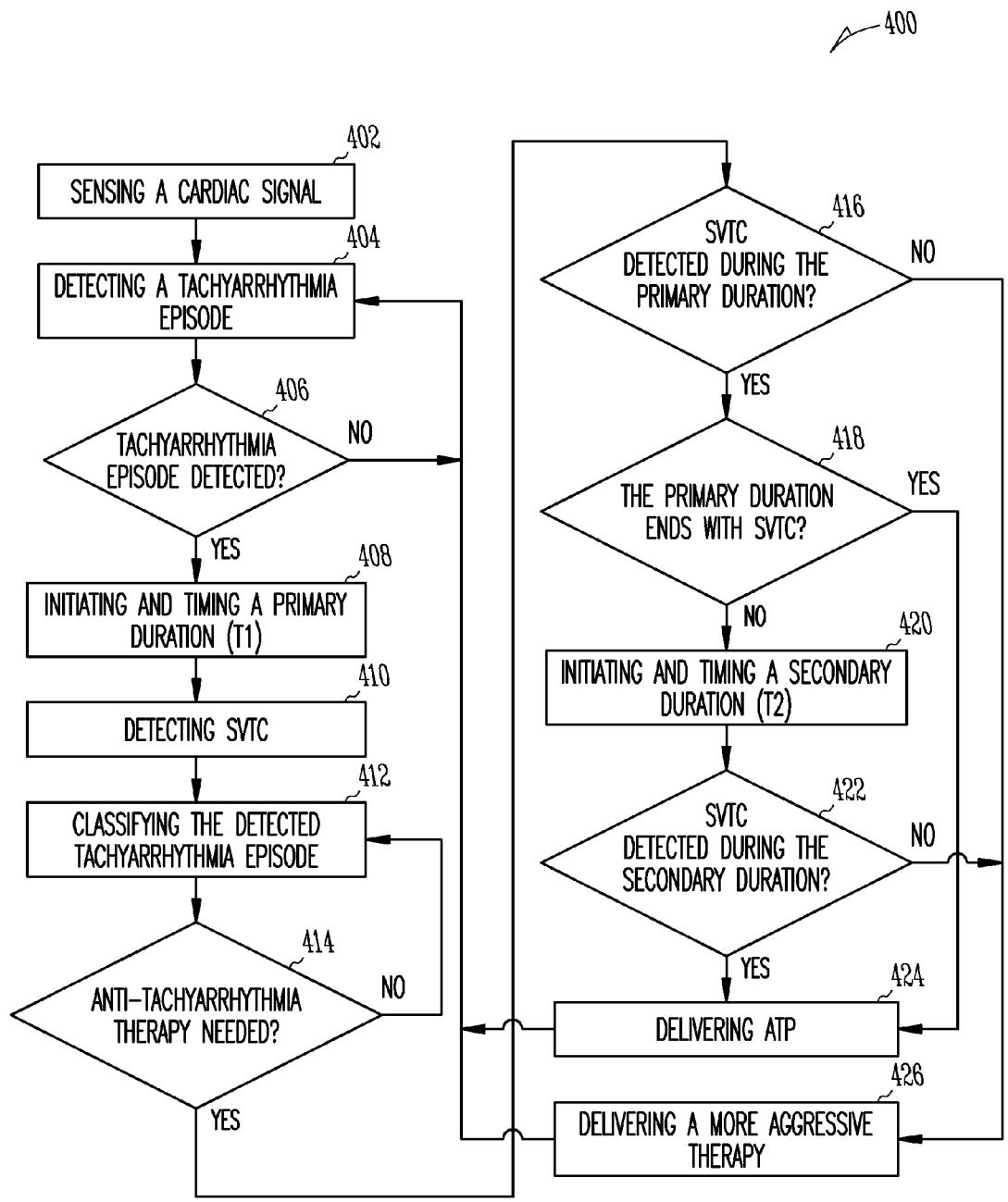
FIG. 4 is a flow chart illustrating an embodiment of a method for selecting and timing anti-tachyarrhythmia therapies using cardiac cycle length stability.

FIG. 4 is a flow chart illustrating an embodiment of a method 400 for selecting and timing anti-tachyarrhythmia therapies using cardiac cycle length stability. In one embodiment, the method is performed by anti-tachyarrhythmia therapy circuit 120, including its various specific embodiments.

A cardiac signal is sensed at 402. A tachyarrhythmia episode is detected from the cardiac signal at 404. In one embodiment, a ventricular electrogram is sensed. Ventricular depolarizations are detected from the ventricular electrogram. Ventricular cycle lengths (also referred to as ventricular intervals) are detected, each as a time interval between two consecutively detected ventricular depolarizations. The detection of a VT episode is declared when the ventricular cycle lengths fall within a VT detection zone defined by one or more tachyarrhythmia detection thresholds.

If the tachyarrhythmia episode is detected at 406, a primary duration (T1) is initiated and timed at 408. In one embodiment, the primary duration is programmed to a value between approximately 1 and 30 seconds, with approximately 5 seconds as a specific example.

SVTCs are detected at 410 as a measure of stability of the cardiac cycle lengths. In one embodiment, SVTCs are detected between the time when the tachyarrhythmia episode is detected and the time when a therapy is delivered or the tachyarrhythmia episode is no longer detected. The SVTCs each include at least a specified minimum number of consecutively detected heart beats (e.g., ventricular depolarizations) over which the cardiac cycle lengths meet a specified stability criterion. An SVTC detection is declared when the specified minimum number of consecutive heart beats have been detected during each of the SVTCs. In one embodiment, the minimum number is programmed to a number between approximately 4 and 8, with approximately 5 being a specific example. In one embodiment, to detect the SVTCs, a cycle-to-cycle variation is calculated. The cycle-to-cycle variation is the difference between cardiac cycle lengths associated with two consecutively detected heart beats. The cycle-to-cycle variation is compared to a predetermined threshold. An SVTC detection is declared when the cycle-to-cycle variation is below the predetermined threshold for the specified minimum number of consecutively detected heart beats. In another embodiment, to detect the SVTCs, a running average of the cardiac cycle lengths is calculated. The cardiac cycle length associated with each of the consecutively detected heart beats are compared to the running average of the cardiac cycle lengths. An SVTC detection is declared when the difference between the cardiac cycle length associated with the each of the consecutively detected heart beats and the running average of the cardiac cycle lengths is within a predetermined margin for the specified minimum number of consecutively detected heart beats. In another embodiment, to detect the SVTCs, a correlation between a morphology of the cardiac signal over each of the detected heart beats and a predetermined template morphology is analyzed. An SVTC detection is declared if the morphology of the cardiac signal over the each of the detected heart beats substantially correlates to the predetermined template morphology for the specified minimum number of consecutively detected heart beats.

The detected tachyarrhythmia episode is classified at 412 as one of predetermined tachyarrhythmia types. In one embodiment, the detected tachyarrhythmia episode is classified as one of VT and SVT. In one embodiment, the classification is performed periodically or continuously when the tachyarrhythmia episode is being detected to confirm the detection of the VT episode.

If the classification of the detected tachyarrhythmia episode indicates that an anti-tachyarrhythmia therapy is needed at 414, at least one SVTC is detected during the primary duration at 416, and the primary duration ends with an SVTC at 418, an ATP therapy is delivered at the end of the primary duration at 424. If the classification of the detected tachyarrhythmia episode indicates that no anti-tachyarrhythmia therapy is needed at 414, the classification at 412 continues as long as the tachyarrhythmia episode is still being detected. If the classification of the detected tachyarrhythmia episode indicates that an anti-tachyarrhythmia therapy is needed at 414, but no SVTC is detected during the primary duration at 416, a more aggressive therapy, such as the cardioversion/defibrillation therapy or the ATP-BC therapy, is delivered at the end of the primary duration at 426. If the classification of the detected tachyarrhythmia episode indicates that an anti-tachyarrhythmia therapy is needed at 414, at least one SVTC is detected during the primary duration at 416, but the primary duration does not end with an SVTC at 418, a secondary duration (T2) is initiated and timed at 420. In one embodiment, the second duration is programmed to a value between approximately 1 and 10 seconds, with approximately 2.5 seconds as a specific example. In another embodiment, the second duration is produced as a function of at least one of a number of SVTCs detected during the primary duration and a size (number of heart beats) of each of the SVTCs detected during the primary duration. The second duration is lengthened for each SVTC detected during the primary duration and/or for each beat detected during each SVTC detected during the primary duration.

If an SVTC is detected during the secondary duration at 422, the ATP therapy is delivered at 424, when the SVTC detection is declared. That is, if one or more SVTCs are detected during the primary duration, the ATP therapy is delivered at the end of the primary duration only if the primary duration ends with an SVTC, but if an SVTC is detected during the secondary duration, the ATP therapy is delivered as soon as the SVTC detection is declared. If no SVTC is detected during the secondary duration at 422, the more aggressive therapy is delivered at 426.

The ATP therapy includes the delivery of at least one burst of pacing pulses. The burst of pacing pulses includes approximately 3 to 10 pacing pulses, with approximately 5 pacing pulses as a specific example, at a pacing rate of approximately 200 to 250 pulses per minute, with approximately 200 pulses per minute as a specific example. The first pacing pulse of the ATP therapy is delivered at the end of a coupling interval that starts with the last intrinsic heart beat, such as represented by the last ventricular depolarization (R wave). In one embodiment, the coupling interval is calculated by using a predetermined number of the cardiac cycle lengths detected during the SVTC. In a specific embodiment, the coupling interval is calculated as a specified percentage of an average of the predetermined number of the cardiac cycle lengths detected during the SVTC.

FIGS. 5-8 illustrate various timing scenarios of how method 400 is applied to detect and treat a tachyarrhythmia. These timing scenarios are presented to illustrate, but not to restrict, how method 400 operates. In all the illustrated scenarios, the primary duration is initiated and timed in response to the detection of a tachyarrhythmia episode, and the minimum number of consecutively detected heart beats required for declaring the detection of an SVTC is 4.

Figure 5:
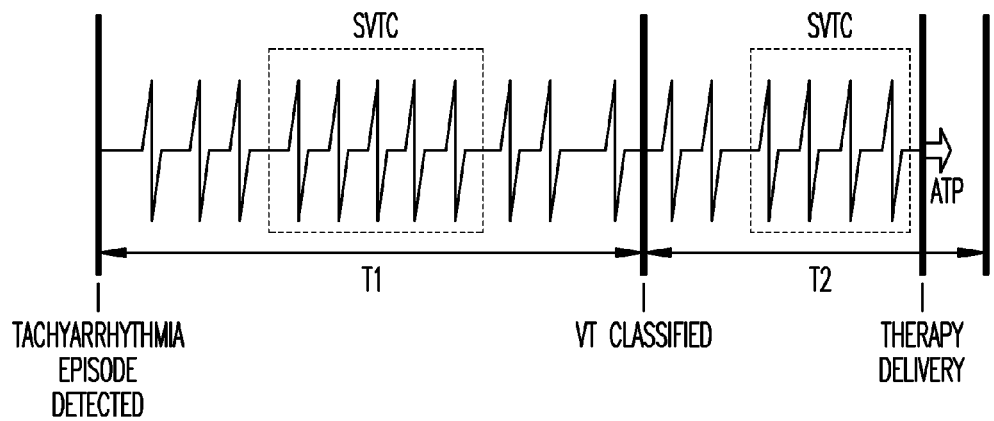
FIG. 5 is an illustration of an example of timing associated with the method of FIG. 4.

In FIG. 5, an SVTC is detected during the primary duration (T1). At the end of the primary duration, the detected tachyarrhythmia episode is classified as VT, but the primary duration does not end with an SVTC. Therefore, the secondary duration (T2) is initiated and timed when the primary duration expires. Another SVTC is detected during the secondary duration. An ATP therapy is delivered as soon as the detection of the SVTC during the secondary duration is declared.

Figure 6:
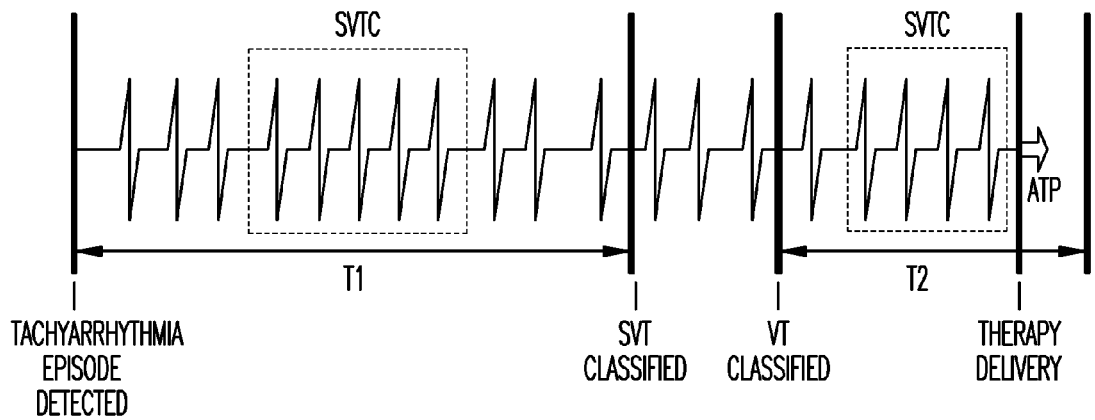
FIG. 6 is an illustration of another example of timing associated with the method of FIG. 4.

In FIG. 6, an SVTC is detected during the primary duration (T1). At the end of the primary duration, the detected tachyarrhythmia episode is classified as SVT. Therefore, the secondary duration (T2) is initiated and timed if and when the detected tachyarrhythmia episode becomes classified as VT. If the classification of detected tachyarrhythmia episode does not become VT, the secondary duration is not initiated, and no therapy delivery is needed. Another SVTC is detected during the secondary duration. An ATP therapy is delivered as soon as the detection of the SVTC during the secondary duration is declared.

Figure 7:
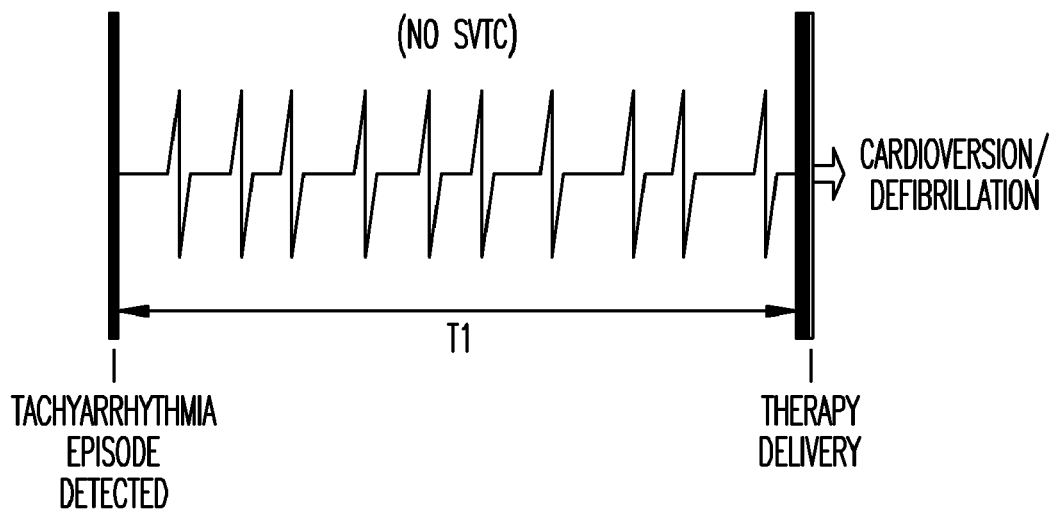
FIG. 7 is an illustration of another example of timing associated with the method of FIG. 4.

In FIG. 7, no SVTC is detected during the primary duration (T1). At the end of the primary duration, the detected tachyarrhythmia episode is classified as VT. Therefore, a cardioversion/defibrillation therapy is delivered following the end of the primary duration.

Figure 8:
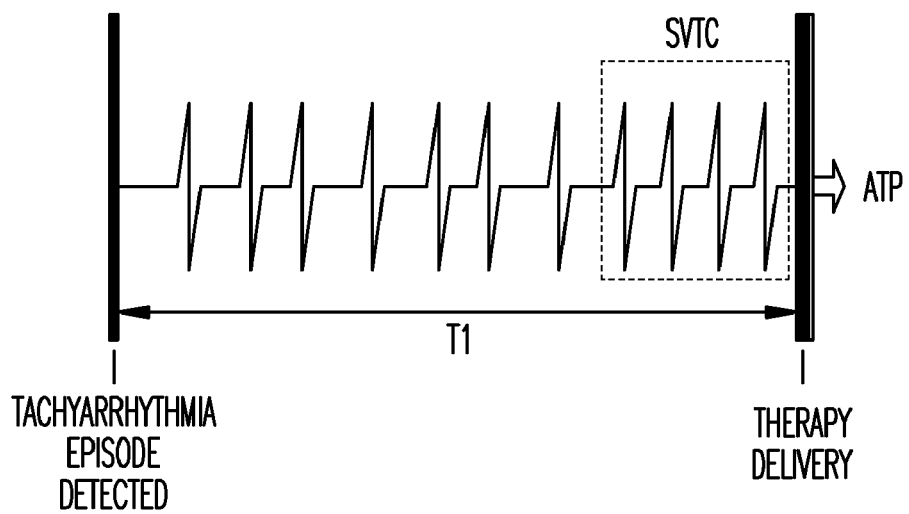
FIG. 8 is an illustration of another example of timing associated with the method of FIG. 4.

In FIG. 8, an SVTC is detected during the primary duration (T1). At the end of the primary duration, the detected tachyarrhythmia episode is classified as VT. The primary duration ends with an SVTC. Therefore, an ATP therapy is delivered at the end of the primary duration.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A method for controlling anti-tachyarrhythmia pacing (ATP), the method comprising:
   sensing a cardiac signal;
   detecting heart beats from the cardiac signal;
   detecting cardiac cycle lengths each being a time interval between two consecutively detected heart beats;
   detecting a tachyarrhythmia episode using the detected cardiac cycle lengths;
   classifying the detected tachyarrhythmia episode;
   initiating a primary duration when the tachyarrhythmia episode is detected;
   analyzing stability of cardiac cycle lengths during the primary duration;
   controlling an initiation of a secondary duration using the stability of cardiac cycle lengths analyzed during the primary duration and the classification of the detected tachyarrhythmia episode;
   analyzing stability of cardiac cycle lengths during the second duration if the secondary duration is initiated, wherein analyzing the stability of cardiac cycle lengths for the primary duration and analyzing the stability of cardiac cycle lengths for the secondary duration each include:
      detecting stable ventricular tachyarrhythmia clusters (SVTCs) from the cardiac signal, the SVTCs each including at least a specified minimum number of consecutively detected heart beats over which the cardiac cycle lengths meet a specified stability criterion; and
      declaring an SVTC detection in response to achieving the specified minimum number of consecutive heart beats over which the cardiac cycle lengths meet a specified stability criterion; and
   controlling a delivery of pacing pulses according to an ATP mode in response to a detected SVTC during the primary duration, a detected SVTC during the secondary duration if the secondary duration is initiated, and the classification of the detected tachyarrhythmia episode.

2. The method of claim 1, wherein:
sensing the cardiac signal comprises sensing a ventricular electrogram;
detecting heart beats comprises detecting ventricular depolarizations as the heart beats from the ventricular electrogram;
detecting cardiac cycle lengths comprises detecting ventricular cycle lengths each being a time interval between two consecutively detected ventricular depolarizations;
detecting the tachyarrhythmia episode comprises declaring a detection of ventricular tachyarrhythmia (VT) when the ventricular cycle length falls within a VT detection zone for a predetermined number or percentage of consecutively detected heart beats; and
classifying the detected tachyarrhythmia episode comprises confirming the declared detection of VT by classifying the detected tachyarrhythmia episode as one of VT and supraventricular tachyarrhythmia (SVT).

3. The method of claim 1, further comprising programming the specified minimum number to a number between approximately 4 and 8.

4. The method of claim 1, wherein detecting the SVTCs comprises calculating a cycle-to-cycle variation being a difference between cardiac cycle lengths associated with two consecutively detected heart beats and comparing the cycle-to-cycle variation to a predetermined threshold, and declaring the SVTC detection comprises declaring the SVTC detection when the cycle-to-cycle variation is below the predetermined threshold for the specified minimum number of consecutively detected heart beats.

5. The method of claim 1, wherein detecting the SVTCs comprises calculating a running average of the cardiac cycle lengths and comparing the cardiac cycle length associated with each of the consecutively detected heart beats to the running average of the cardiac cycle lengths, and declaring the SVTC detection comprises declaring the SVTC detection when a difference between the cardiac cycle length associated with the each of the consecutively detected heart beats and the running average of the cardiac cycle lengths is within a predetermined margin for the specified minimum number of consecutively detected heart beats.

6. The method of claim 1, wherein detecting the SVTCs comprises analyzing a correlation between a morphology of the cardiac signal over each of the detected heart beats and a predetermined template morphology, and declaring the SVTC detection comprises declaring the SVTC detection when the morphology of the cardiac signal over the each of the detected heart beats substantially correlates to the predetermined template morphology for the specified minimum number of consecutively detected heart beats.

7. The method of claim 1, wherein controlling the initiation of the secondary duration comprises initiating the secondary duration when the primary duration expires if the tachyarrhythmia is classified as VT when the primary duration expires and the stable SVTC detector declares at least one SVTC detections during the primary duration but the primary duration does not expire with any of the detected SVTCs.

8. The method of claim 7, wherein controlling the initiation of the secondary duration comprises initiating the secondary duration when the tachyarrhythmia is classified as VT if the tachyarrhythmia is classified as VT after the primary duration expires and the stable SVTC detector declares at least one SVTC detections during the primary.

9. The method of claim 8, further comprising:
programming the primary duration to value between approximately 1 and 30 seconds; and
programming the second duration to a value between approximately 1 and 10 seconds.

10. The method of claim 8, further comprising producing the second duration based on at least one of a number of SVTCs detected during the primary duration and a size of each of the SVTCs detected during the primary duration.

11. The method of claim 1, wherein controlling the delivery of the pacing pulses according to the ATP mode comprises initiating the delivery of the pacing pulses according to the ATP mode when the primary duration expires if the tachyarrhythmia is classified as VT when the primary duration expires and the primary duration expires with an SVTC, the ATP therapy including a delivery of at least one burst of pacing pulses.

12. The method of claim 11, wherein controlling the delivery of the pacing pulses according to the ATP mode comprises initiating the delivery of the pacing pulses according to the ATP mode when a detection of SVTC is declared during the secondary duration if the tachyarrhythmia is classified as VT when the SVTC is detected during the secondary duration.

13. The method of claim 12, further comprising calculating a coupling interval (CI) using a predetermined number of the cardiac cycle lengths detected during the SVTC.

14. The method of claim 1, further comprising controlling a delivery of cardioversion/defibrillation therapy using the stability of cardiac cycle lengths analyzed during the primary duration, the cardiac cycle lengths during the secondary duration if the secondary duration is initiated, and the classification of the detected tachyarrhythmia episode.

15. The method of claim 14, further comprising controlling the delivery of cardioversion/defibrillation therapy comprises initiating the delivery of cardioversion/defibrillation therapy if the tachyarrhythmia is classified as VT when the primary duration expires and no SVTC is detected during the primary duration.

16. The method of claim 15, further comprising controlling the delivery of cardioversion/defibrillation therapy comprises initiating the delivery of a cardioversion/defibrillation therapy if the tachyarrhythmia is classified as VT when the second duration expires and no SVTC is detected during the second duration.

17. An implantable medical device, comprising:
a sensing circuit configured to sense a cardiac signal;
a pacing output circuit configured to deliver pacing pulses;
a beat detector, coupled to the sensing circuits and configured to detect heart beats from the cardiac signal;
a cycle length detector, coupled to the beat detector and configured to detect cardiac cycle lengths each being a time interval between two consecutively detected heart beats;
a tachyarrhythmia detector, coupled to the cycle length detector and configured to detect a tachyarrhythmia episode using the cardiac cycle lengths and one or more tachyarrhythmia detection thresholds;
a tachyarrhythmia classifier, coupled to the tachyarrhythmia detector and configured to classify the detected tachyarrhythmia episode;
a primary duration timer, coupled to the tachyarrhythmia detector and configured to initiate a primary duration in response to the detection of the tachyarrhythmia episode;
a cycle length stability analyzer, coupled to the sensing circuit and configured to analyze stability of the detected cardiac cycle lengths, the cycle length stability analyzer including a stable ventricular tachyarrhythmia cluster (SVTC) detector configured to detect SVTCs from the cardiac signal, the SVTCs each including at least a specified minimum number of consecutively detected heart beats over which the cardiac cycle lengths meet a specified stability criterion;

a secondary duration timer coupled to the primary duration timer and the cycle length stability analyzer, the secondary duration timer configured to control an initiation of a secondary duration using the stability of cardiac cycle lengths analyzed during the primary duration and the classification of the detected tachyarrhythmia episode, the secondary duration to be initiated in response to expiration of the primary duration; and an anti-tachyarrhythmia pacing (ATP) controller coupled to the primary duration timer, the cycle length stability analyzer, the secondary duration timer, and the pacing output circuit, the ATP controller configured to control the delivery of the pacing pulses according to an ATP mode in response to a detected SVTC during the primary duration, a detected SVTC during the secondary duration if the secondary duration is initiated, and the classification of the detected tachyarrhythmia episode.

18. The implantable medical device of claim 17, wherein the tachyarrhythmia classifier is configured to classify the detected tachyarrhythmia episode as one of tachyarrhythmia types including ventricular tachyarrhythmia (VT) and supraventricular tachyarrhythmia (SVT).

19. The implantable medical device of claim 18, wherein the sensing circuit is configured to sense a ventricular electrogram, the beat detector is configured to detect ventricular depolarizations as the heart beats from the ventricular electrogram, the cycle length detector is configured to detect ventricular cycle lengths each being a time interval between two consecutively detected ventricular depolarizations, the tachyarrhythmia detector is configured to declare a detection of a VT episode when the ventricular cycle length falls within a VT detection zone for a predetermined number or percentage of consecutively detected heart beats, and the tachyarrhythmia classifier is configured to confirm the detection of the VT episode.

20. The implantable medical device of claim 17, wherein the cycle length stability analyzer is configured to calculate a running average of the cardiac cycle lengths and determine whether a difference between the cardiac cycle length associated with each of the consecutively detected heart beats and the running average of the cardiac cycle lengths is within a specified margin for the specified minimum number of consecutively detected heart beats.

21. The implantable medical device of claim 17, wherein the cycle length stability analyzer is configured to analyze a correlation between a morphology of the cardiac signal over each of the detected heart beats and a predetermined template morphology and determine whether the morphology of the cardiac signal over the each of the detected heart beats substantially correlates to the predetermined template morphology for the specified minimum number of consecutively detected heart beats.

* * * * *

UNITED STATES PATENT AND TRADEMARK OFFICE
CERTIFICATE OF CORRECTION

| | | |
|---|---|---|
| PATENT NO. | : 8,050,758 B2 | Page 1 of 1 |
| APPLICATION NO. | : 12/829218 | |
| DATED | : November 1, 2011 | |
| INVENTOR(S) | : Dan Li | |

It is certified that error appears in the above-identified patent and that said Letters Patent is hereby corrected as shown below:

In column 13, line 64, in Claim 8, delete "primary." and insert -- primary duration. --, therefor.

Signed and Sealed this
Thirty-first Day of January, 2012

David J. Kappos
*Director of the United States Patent and Trademark Office*